US00PP12792P2

(12) United States Plant Patent
Verwer

(10) Patent No.: US PP12,792 P2
(45) Date of Patent: Jul. 23, 2002

(54) DAHLIA PLANT NAMED 'MELODY GIPSY'

(75) Inventor: Aad W. M. Verwer, Lisse (NL)

(73) Assignee: Fa. Gebr. Verwer, Lisse (NL)

( * ) Notice: Subject to any disclaimer, the term of this patent is extended or adjusted under 35 U.S.C. 154(b) by 0 days.

(21) Appl. No.: 09/550,661

(22) Filed: Apr. 17, 2000

(51) Int. Cl.[7] ..... A01H 5/00
(52) U.S. Cl. ..... Plt./321
(58) Field of Search ..... Plt./321

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Dahlia plant named 'Melody Gipsy', characterized by its upright, somewhat outwardly spreading and uniform plant habit; freely branching habit; dark green foliage; freely flowering habit; semi-cactus inflorescence form with inflorescences positioned above the foliage; pink and yellow bi-colored ray florets; and excellent garden performance.

2 Drawing Sheets

BACKGROUND OF THE INVENTION

The present Invention relates to a new and distinct cultivar of Dahlia plant, botanically known as *Dahlia hybrida* and hereinafter referred to by the name 'Melody Gipsy'.

The new Dahlia is a product of a planned breeding program conducted by the Inventor in Lisse, The Netherlands. The objective of the breeding program is to create new Dahlia cultivars with uniform growth habit, decorative inflorescence form, attractive ray floret colors, and good inflorescence longevity.

The new Dahlia originated from a cross pollination made by the Inventor in 1997 of the *Dahlia hybrida* cultivar VDW 57, not patented, as the female, or seed, parent with the *Dahlia hybrida* cultivar Alfred Grille, not patented, as the male, or pollen, parent. The new Dahlia was discovered and selected by the Inventor as a single flowering plant within the progeny of the stated cross grown in a controlled environment in Lisse, The Netherlands, in 1997. The selection of this plant was based on its uniform plant habit and attractive ray floret coloration.

Asexual reproduction of the new Dahlia by cuttings was first conducted in Lisse, The Netherlands. Asexual reproduction by cuttings has shown that the unique features of this new Dahlia are stable and reproduced true to type in successive generations.

SUMMARY OF THE INVENTION

The cultivar 'Melody Gipsy' has not been observed under all possible environmental conditions. The phenotype may vary somewhat with variations in environment such as temperature, daylength, light intensity, water and nutritional status without, however, any variance in genotype.

The following traits have been repeatedly observed and are determined to be the unique characteristics of 'Melody Gipsy'. These characteristics in combination distinguish 'Melody Gipsy' as a new and distinct Dahlia:

1. Upright, somewhat outwardly spreading and uniform plant habit.
2. Freely branching habit, full and dense plants.
3. Dark green foliage.
4. Freely flowering habit.

5. Semi-cactus inflorescence form with inflorescences positioned above the foliage.
6. Pink and yellow bi-colored ray florets.
7. Excellent garden performance.

Compared to plants of the female parent, the cultivar VDW 57, plants of the new Dahlia are more compact, have larger inflorescences, are more freely flowering, and differ in ray floret coloration as plants of the cultivar VDW 57 have orange-colored ray florets. Compared to plants of the male parent, the cultivar Alfred Grille, plants of the new Dahlia are more compact, are more freely flowering and have longer-lasting inflorescences.

Plants of the new Dahlia can be compared to plants of the Dahlia cultivar Park Princess, not patented. In side-by-side comparisons conducted by the Inventor in Lisse, The Netherlands, plants of the new Dahlia were more freely branching, were bushier, and had larger and longer lasting inflorescences than plants of the cultivar Park Princess.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph on the first sheet comprises a side perspective view of typical flowering plants of 'Melody Gipsy' that were about four months old.

The photograph on the second sheet comprises a close-up view of typical inflorescences of 'Melody Gipsy'.

DETAILED BOTANICAL DESCRIPTION

In the following description, color references are made to The Royal Horticultural Society Colour Chart except where general terms of ordinary dictionary significance are used. The afore-mentioned photographs and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 23° C. and night temperatures ranged between 10 and 15° C. Measurements and numerical values represent averages of typical flowering plants that were about four months old.

Botanical classification: *Dahlia hybrida* cultivar Melody Gipsy.

Parentage:

*Female, or seed, parent.*—*Dahlia hybrida* cultivar VDW 57, not patented.

*Male, or pollen, parent.*—*Dahlia hybrida* cultivar Alfred Grille, not patented.

Propagation:

*Type.*—By vegetative cuttings.

*Time to initiate roots.*—About 3 to 6 days at 16° C.

*Time to develop roots.*—About 14 days at 16° C.

*Root description.*—Fine, fibrous and well-brached.

Plant description:

*Appearance.*—Herbaceous flowering container or garden plant. Inverted triangle; stems mostly upright and somewhat outwardly spreading giving a rounded appearance to the plant. Freely branching, about 9 lateral branches develop after removal of terminal apex (pinching); dense and full plants.

*Crop time.*—About 75 days from planting are required to produce flowering finished plants.

*Plant height.*—About 70 cm.

*Plant width.*—About 40 cm.

*Lateral branches (peduncles).*—Angle: Mostly erect. Strength: Strong. Length: About 25 cm. Diameter: At base: About 1.2 cm. At mid-section: About 7.6 mm. At apex, just below the inflorescence: About 3.9 mm. Texture: Smooth, glabrous. Color: Towards base, 146B; towards apex, 144B.

*Foliage description.*—Arrangement: Leaves opposite; leaves may be single or compound with three or five leaflets. Typically about 7 pairs of leaves per lateral stem. Shape: Ovate. Apex: Acuminate. Base: Attenuate. Margin: Serrate. Length: Single leaves: About 25 cm. Compound leaflets: About 12 cm. Width: Single leaves: About 7.8 cm. Compound leaflets: About 7 cm. Venation pattern: Pinnate. Texture: Smooth, glabrous; leathery. Color: Young foliage, upper surface: Close to 137A. Young, lower surface: Close to 146A. Mature foliage, upper surface: Close to 147A or darker than 147A. Mature foliage, lower surface: Close to 147B. Venation, upper surface: Close to 151A. Venation, lower surface: Close to 146B. Petiole length: About 6 cm. Petiole color: Upper surface: 146C. Lower surface: 146B.

Inflorescence description:

*Appearance.*—Ternimal inflorescences held above the foliage on strong peduncles. Semi-cactus inflorescence form with elongated ovate-shaped ray florets; ray florets arranged acropetally on a capitulum. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 15 to 20 days in an outdoor environment; and as cut flowers, inflorescences maintain good color and substance for about 7 days in an indoor environment.

*Quantity of inflorescences.*—One per lateral shoot, about 48 inflorescences plant develop during the growing season, summer through autumn.

*Inflorescence bud, at stage of showing color.*—Shape: Globular to ovoid/conical. Length: About 1.2 cm. Diameter: About 1.2 cm. Color: Close to 154A.

*Inflorescences.*—Shape, in profile: Hemispherical. Diameter: About 12 cm. Depth (height): About 8.5 cm.

*Ray florets.*—Shape: Elongated ovate. Apex: Acute. Base: Attenuate; short corolla tube. Margin: Entire. Length: About 5.5 cm. Width: About 1.6 cm. Texture: Smooth, glabrous; satiny. Number of ray florets per inflorescence: More than 200. Color: When opening, upper and lower sufaces: Close to 62A. Fully opened, upper surface: Towards base, 14D; mid-section, closest to 62D; towards apex and at margin, 68D. Fully opened, lower surface: Towards base, 10C; towards apex, 62C.

*Disc florets.*—Number of disc florets per inflorescence: About 23. Shape: Tubular, elongated. Apex: Five-pointed.

*Phyllaries.*—Quantity: One whorl of about 5 or 6 phyllaries. Shape: Ovate. Apex: Acute. Base: Attenuate. Margin: Entire. Length: About 1.9 cm. Width: About 9.9 mm. Texture: Smooth. Color: Upper surface: Close to 146B. Lower surface: Close to 146A.

*Reproductive organs.*—Androecium: Present on disc florets only. Stamen quantity: About 5 per floret. Anther length: About 4.4 mm. Anther color: Close to 9A. Pollen amount: Scarce. Pollen color: 23A. Gynoecium: Present on ray and disc florets. Pistil quantity: One per floret. Stigma color: Close to 5A. Style length: About 1.2 cm. Style color: Close to 154A.

*Seeds.*—Seed development has not been observed to date.

Disease/pest resistance: Resistance to pathogens and pests common to Dahlias has not been observed on plants grown under commercial greenhouse or outdoor conditions.

Temperature tolerance: Plants of the new Dahlia have been observed to be tolerant temperatures from 0 to 40° C.

It is claimed:

1. A new and distinct cultivar of Dahlia plant named 'Melody Gipsy', as illustrated and described.

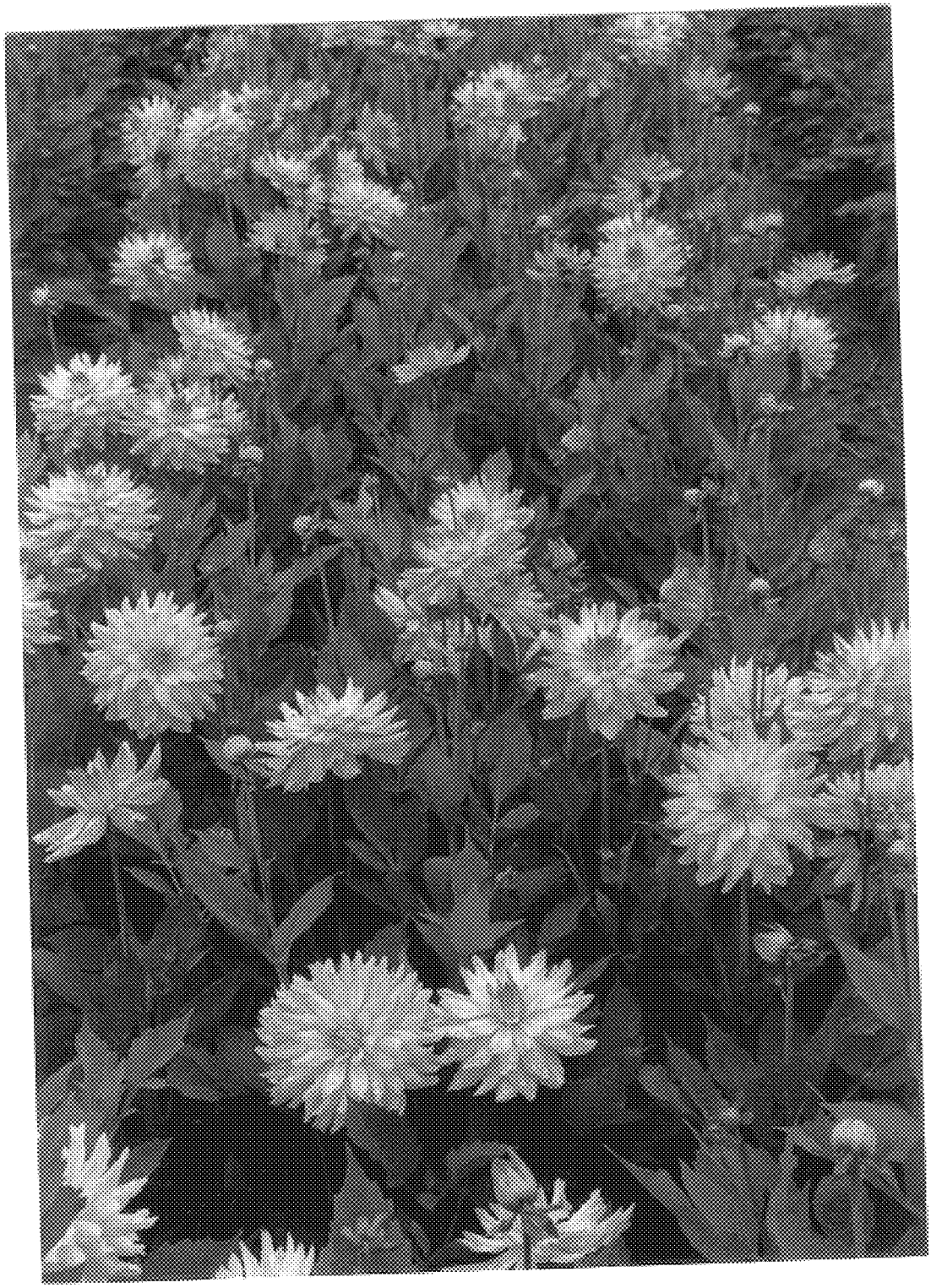

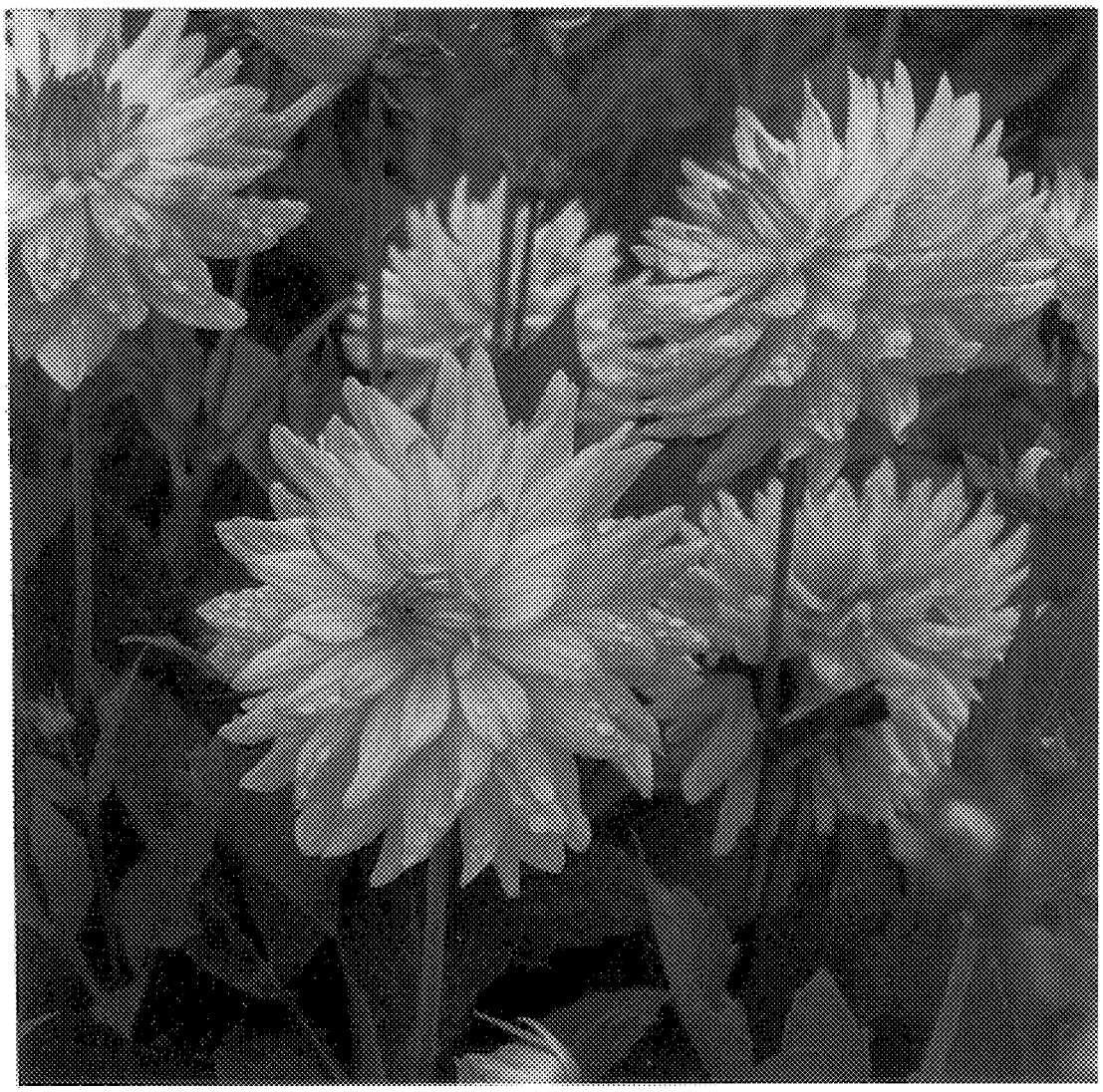

* * * * *